United States Patent
Maiti

(10) Patent No.: US 7,820,171 B2
(45) Date of Patent: Oct. 26, 2010

(54) USE OF AVIAN ANTI-METHANOGEN ANTIBODIES FOR REDUCTION OF METHANE PRODUCTION

(76) Inventor: Pradip Maiti, 6-62 Scurfield Blvd., Winnipeg, MB (CA) R3Y 1M5

( * ) Notice: Subject to any disclaimer, the term of this patent is extended or adjusted under 35 U.S.C. 154(b) by 105 days.

(21) Appl. No.: 12/102,066

(22) Filed: Apr. 14, 2008

(65) Prior Publication Data

US 2008/0254129 A1 Oct. 16, 2008

Related U.S. Application Data

(60) Provisional application No. 60/911,359, filed on Apr. 12, 2007.

(51) Int. Cl.
*A61K 39/395* (2006.01)
*A61K 39/40* (2006.01)
*A61K 9/14* (2006.01)

(52) U.S. Cl. .................. 424/164.1; 424/130.1; 424/489

(58) Field of Classification Search ........................ None
See application file for complete search history.

(56) References Cited

U.S. PATENT DOCUMENTS 6,365,158 B1 * 4/2002 Williams et al. ......... 424/190.1
2003/0003104 A1 * 1/2003 Mottola et al. ........... 424/164.1
2004/0120944 A1 * 6/2004 Hunchar et al. .......... 424/130.1
2006/0233825 A1 * 10/2006 Jayappa et al. ........... 424/190.1

OTHER PUBLICATIONS

Whitford et al. BMC Microbiology (2001) 1:5.*
Schade et al. ATLA Apr. 2005; 33 (2): 129-154.*
Finlay et al. Applied and Environmental Microbiology, May 2006, p. 3343-3349.*
Fricke et al. Journal of Bacteriology, Jan. 2006, p. 642-658.*

* cited by examiner

*Primary Examiner*—N. M. Minnifield
*Assistant Examiner*—Oluwatosin Ogunbiyi
(74) *Attorney, Agent, or Firm*—Michael R. Williams

(57) ABSTRACT

Herein, it is shown that strong specific anti-methanogen avian antibodies can be produced when chickens are immunized with an optimal dose of methane producing bacterial antigen (methanogen) formulated with an appropriate adjuvant. The antibodies can in turn be used to reduce methane gas production from an animal by administering an effective amount of the anti-methanogen antibodies to the animal, thereby reducing methane gas evolved by the animal compared to an untreated or mock treated control animal of similar age and condition.

2 Claims, 4 Drawing Sheets

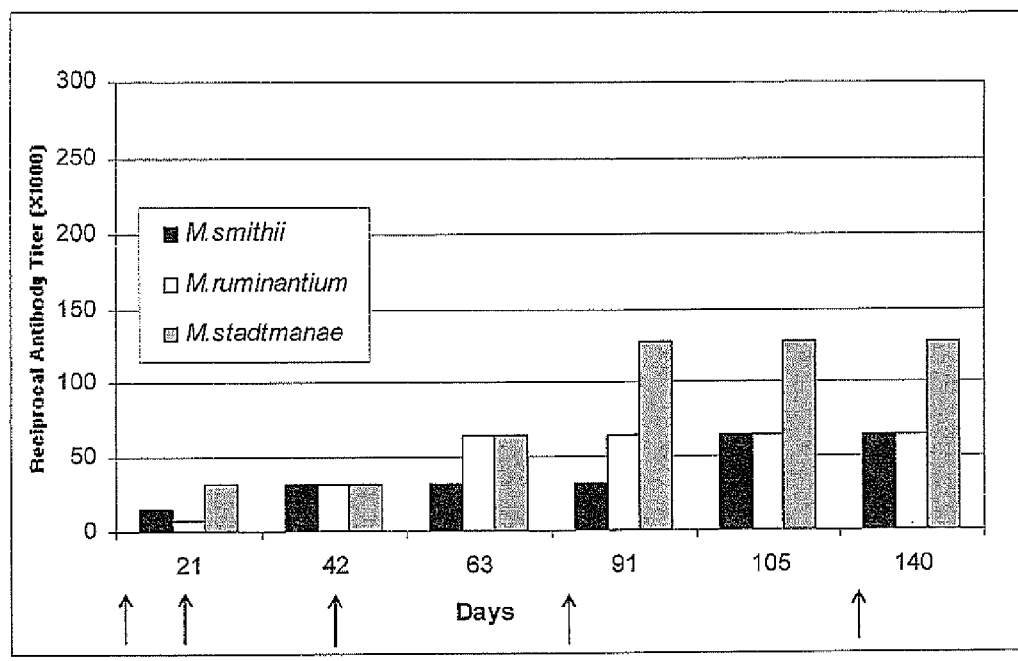
1A    Figure 1
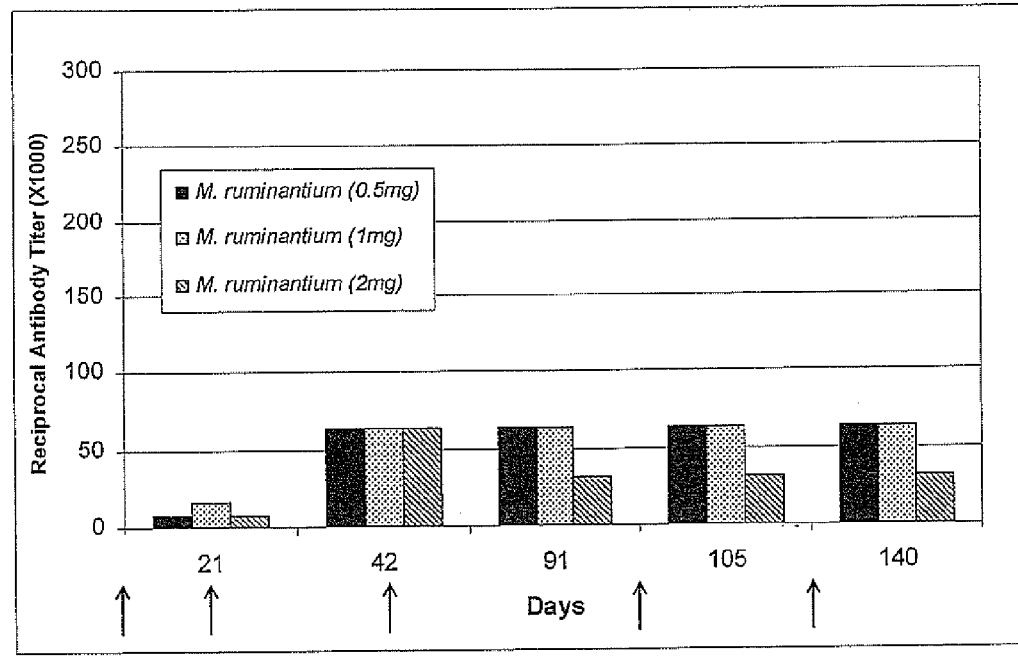
1B    Figure 1

USE OF AVIAN ANTI-METHANOGEN ANTIBODIES FOR REDUCTION OF METHANE PRODUCTION

PRIOR APPLICATION INFORMATION

The instant application claims the benefit of U.S. Provisional Patent Application 60/911,359, filed Apr. 12, 2007.

BACKGROUND OF THE INVENTION

According to a recent report published by the United Nations Food and Agriculture Organization, the livestock is found to be a major threat to environment, as the sector is responsible for 18% green house gas emissions. The livestock sector emits 37% of anthropogenic methane that has 23 times more global warming potential than $CO_2$ (1). Cattle and other ruminant animals produce methane in normal fermentation process, when microorganisms in their stomach break down fibers in grasses and grains they eat. The microorganisms that produce methane in ruminant fermentation are a distinct group of Methanogenic bacteria, called methanogens (2-4). An estimated 12-30% of total atmospheric methane is produced by ruminants (5). Besides having a significant impact on global warming, methane formation also represents up to 15% loss of dietary energy to the ruminant (6). Therefore, there is an urgent need to develop strategies to curtail ruminal methane emissions and improve animal performance, which will have both ecological impact as well as economic benefit.

Several strategies including chemical suppression and biotechnological interventions have been investigated to attenuate methane production and improve feed efficiency (7-9). However, there is growing concern over the use of chemical inhibitors in animals used for human consumptions, and possibility in developing chemical resistant methanogens, researchers are now focusing on developing biological strategies to solve the problem (10). Recently, it was reported that immunization of sheep with a methanogen vaccine demonstrated a minor reduction (7.7%) of methane emissions (11).

For targeting microorganisms, our laboratories have been developing passive antibody therapy approach using avian antibody technology to control gastrointestinal disease and to improve the growth performance. In earlier studies, we have shown that avian antibodies targeted to *E. coli* 0157:H7 were capable of reducing the shedding of *E. coli* 0157:H7 from sheep (13). Also, the avian antibodies targeted to the virulent factors of *E. coli* 0157:H7 were shown to inhibit attachment of *E. coli* 0157:H7 to the host cells and to block colonization of *E. coli* 0157:H7 (14), Furthermore, avian antibodies targeted to *E. coli* K-88, were demonstrated to inhibit proliferation of *E. coli* K-88, to block adherence to the host cells and confer protection to piglets experimentally challenged with ETEC K-88 (15). A number of researchers also have shown that IgY antibodies can be used for passive immunization or treatment of animals suffering from various bacterial and viral diseases (18-21). Furthermore, the yolk of eggs from laying hens immunized with the target antigen is shown to be an inexpensive and convenient source for polyclonal antibodies. Chickens produce three principal immunoglobulin (Ig) classes, IgM, IgA and IgG, and the functional homologue of mammalian IgG is IgY (16, 17). However, there has been no report to date on the generation of avian antibodies against methanogens and their effect on reduction of methane production. Therefore, the aim of this study was two-fold, to generate strong avian antibodies targeted to a group of the three predominant methanogens of ruminant fluid and to investigate the role of avian antibodies directed against the methanogens on ruminant methane production in vitro.

SUMMARY OF THE INVENTION

According to a first aspect of the invention, there is provided a method of reducing methane gas production from an animal comprising administering to said animal an effective amount of anti-methanogen antibodies, thereby reducing methane gas evolved by said animal compared to an untreated or mock treated control animal of similar age and condition.

According to a second aspect of the invention, there is provided a method of reducing methane gas production from a ruminant animal comprising administering to said animal an effective amount of egg powder comprising anti-*M. stadtmaniae* antibodies, thereby reducing methane gas evolved by said animal compared to an untreated or mock treated control animal of similar age and condition.

Figure 1:
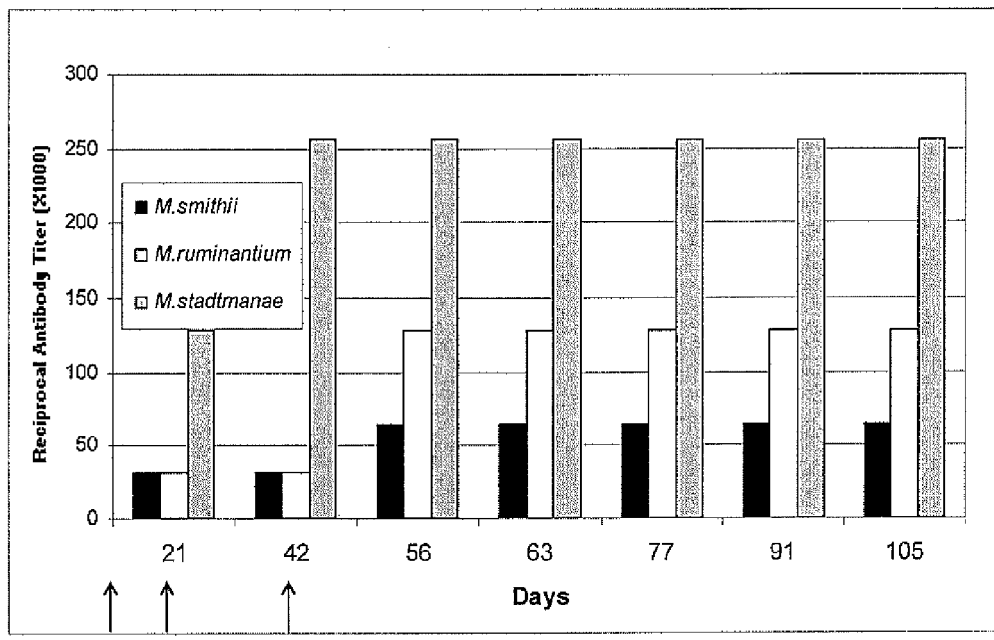
FIG. 1. Induction of avian antibody responses to methanogenic antigens, *M. smithii M. ruminantium* and *M stadtmaniae*. Chickens were immunized with methanogen formulated with CFA/IFA (1A), with Quil A (1B) and with MONTANIDE ISA 70 (mineral oil adjuvant) (1C) on days 0, 21, 42, 84 & 133 for 1A and 1B and 0, 21, & 42, as indicated by ↑. Anti-methanogen antibodies expressed as end point titer on days post primary immunization.

Table 1: Effects of semi-purified specific anti-methanogen IgY antibodies on fermentation characteristics of in vitro ruminal batch culture. n=3 (Trial 1)

Table 2. Measurement of the cross-reactivity between *M. ruminantium*, *M. smithii* and *M. stadtmaniae* by ELISA Table 3. Quantitative estimation of relatedness between the three methanogens determined with absorbed antibodies Table 4. ELISA Reactivity of anti-methanogen antibodies to methanogens in ruminant fluid.

Table 5: Effects of 0.6 g of egg powder containing specific anti-methanogen antibodies on fermentation characteristics of in vitro ruminal batch culture. n=3 (Trial 2).

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

As can be seen below, the results demonstrate that strong specific anti-methanogen avian antibodies can be produced when chickens are immunized with an optimal dose of methane producing bacterial antigen (methanogen) formulated with an appropriate adjuvant. Among the three adjuvant evaluated, the strongest and long lasting antibody responses to methanogens were achieved with MONTANIDE ISA 70 (mineral oil adjuvant), followed by CFA/IFA (complete Freund adjuvant and incomplete Freund adjuvant) and Quil A (saponin derivative). Of the three methanogens used as antigens, the strongest antibody responses were induced with *M. stadtmaniae* followed by *M. ruminantium* and *M. smithii*. Also, anti-methanogen antibodies were determined to be highly cross-reactive, and the anti-*M. stadtmaniae* antibodies were shown to the most cross-reactive followed by *M. smithii* and *M. ruminantium*.

According to a first aspect of the invention, there is provided a method of reducing methane gas production from an animal comprising administering to said animal an effective amount of anti-methanogen antibodies, thereby reducing methane gas evolved by said animal compared to an untreated or mock treated control animal of similar age and condition.

Preferably, the anti-methanogen antibodies are IgY antibodies isolated from eggs from hens immunized with a methanogen antigen. Preferably, the anti-methanogen antibodies are in the form of a dried powder, as discussed below.

The powder may be a mixture of antibodies from eggs from hens immunized with different methanogen antigens, for example, antigens from *M. stadtmaniae, M. ruminantium* and *M. smithii*.

Preferably, the eggs are from hens immunized with at least one *M. stadtmaniae* antigen. Preferably, the antigen is administered with an adjuvant selected from the group consisting of MONTANIDE ISA 70 (mineral oil adjuvant), CFA/IFA and Quil A. More preferably, the adjuvant is MONTANIDE ISA 70 (mineral oil adjuvant).

Preferably, the powder has a titer of at least 1:64000, as discussed below.

As will be appreciated by one of skill in the art, the untreated or mock treated control does not necessarily have to be repeated each time. As discussed below, the control may be fed egg powder from non-immunized hens or egg powder from hens immunized with non-methanogen antigens.

The animal may be a ruminant animal.

According to a second aspect of the invention, there is provided a method of reducing methane gas production from a ruminant animal comprising administering to said animal an effective amount of egg powder comprising anti-*M. stadtmaniae* antibodies, thereby reducing methane gas evolved by said animal compared to an untreated or mock treated control animal of similar age and condition.

Preferably, the anti-methanogen antibodies are IgY antibodies isolated from eggs from hens immunized with a methanogen antigen. Preferably, the anti-methanogen antibodies are in the form of a dried powder, as discussed below.

The powder may be a mixture of antibodies from eggs from hens immunized with different methanogen antigens.

Preferably, the eggs are from hens immunized with at least one *M. stadtmaniae* antigen. Preferably, the antigen is administered with an adjuvant selected from the group consisting of MONTANIDE ISA 70 (mineral oil adjuvant), CFA/IFA and Quil A. More preferably, the adjuvant is MONTANIDE ISA 70 (mineral oil adjuvant).

Preferably, the powder has a titer of at least 1:64000, as discussed below.

The results from our initial trial with purified anti-methanogen IgY antibodies demonstrated that low concentrations of purified antibodies have no effect on methanogenesis or normal ruminal fermentation in batch culture conditions, compared to the antibody control. In this trial, 4 mg of purified IgY antibodies, purified from eggs of chickens immunized with methanogens formulated with CFA/IFA, and the same concentration of IgY purified from eggs of un-immunized chickens, were used for evaluation of antibody function.

It was possible that the initial experiment failed because the antibody concentration might not have been high enough or proportion of specific antibodies to particular cell-surface antigen may have been insufficient or the purified avian antibodies might have been denatured in ruminant fermentation process or the target methanogens were lacking in the ruminant fluid. These findings prompted us to modify our antibody generation technique to produce high titer anti-methanogen antibodies, evaluate the cross-reactivity and reassess the effects of higher concentration of avian antibodies in an egg powder matrix instead of purified antibodies. Using the revised approach, we observed a significant reduction in methane production by three treatments, anti-*M. stadtmaniae* antibody, anti-*M. smithii* antibody and a combination of the three antibodies at 12-hour post-treatment, when compared with the antibody control. However, when compared with the PBS control, there was a significant difference in reduction of methane production at 6, 12 and 24-hour post-treatment using anti-methanogen antibodies as well as antibody control (egg powder prepared from non immunized eggs). Originally, the study was designed to determine if a combination of the three anti-methanogen treatment could be an effective strategy to reduce methane emissions. The results demonstrated that the maximum reduction in methane production was achieved with the treatment of ruminant fluid with the three anti-methanogen combination in in vitro fermentation.

A direct comparison between the negative control (no egg powder) and the treatment controls (non-immune egg powder) indicated a significant response in virtually all fermentation measures, including methane production. The physical presence of this additional substrate, containing predominantly protein, undoubtedly contributed to this divergence. Additionally, previous reports have shown that egg powder alone has distinct anti-bacterial properties. Nevertheless, these observations do not negate the differences in the treatments compared with the non-immune controls, which indicate a direct response to specific antibodies.

Wright et al. conducted an in vivo assessment of two formulations of methanogen vaccines in sheep to reduce methane emissions. They reported that of two vaccines tested, the formulation with fewer antigenic targets resulted in a significant (7.7%) reduction of methane emissions compared with a control group. The authors speculate that the significant decrease in methane emissions observed were due to specific activity anti-methanogen secretory antibodies delivered to the rumen via saliva. Thus, a novel adaptation of this approach, passive immunization, may achieve the similar or better results with unique advantages such as the ability to control the quantity and quality of antibodies administered. Additionally, passive delivery of antibodies will prevent some of the adverse reactions observed in response to immunizations, including temporary reduction to the animal's liveweight and local reactions at the site of immunization. The experimental approach described here may also provide a useful means to evaluate antigenic targets for future vaccine formulations.

Though the ultimate aim of our analyses was to determine whether antibodies could effectively inhibit methane production, we also examined the effects of the antibody treatments on normal digestive fermentation. An ideal treatment to inhibit methanogenesis would be one that is effective in reducing $CH_4$ production without decreasing VFA production or ruminal microbial N synthesis. Ruminal VFA and $CH_4$ production in vitro correlate strongly with the C2:C3 ratio, which is dependant on pH and substrate. In trial 2, α-RUM decreased methane production at 12 h of incubation but it also negatively affected total VFA production in the end of the incubation (24 h), even though cumulative GP and in vitro digestibility were not affected compared to control. Ideally, egg powder containing α-STAD antibodies and antibody combo decreased methanogenesis but did not affect products of digestion, GP or IVDMD.

We observed significantly less ammonia accumulation ($P \leq 0.003$) in only the treatments exhibiting repressed methane synthesis at 12 h. This may suggest ammonia production was concurrently suppressed, or may be evidence of increased uptake of nitrogen for microbial protein synthesis. Increased production of ammonia due to excess protein may have served as a hydrogen sink, thereby preventing methanogenesis. As expected, the treatment groups, including the control had substantially more ammonia accumulation by 24 h compared with the negative control, likely due to the increased protein digestion. Remarkably, the increased accumulation of ammonia was not evident until 24 h, supporting the conclusion that it was immunogenic activity of the specific antibodies, not excess ammonia, responsible for the decrease in methane concentrations at 12 h.

Methanogens are obligate anaerobes and are fastidious to culture in laboratory conditions. Consequently, it is well recognized that our repertoire of culturable species may not represent the diversity of the ruminant's resident methanogen population. Molecular analyses estimating phylogenetic diversity of ruminant methanogens have revealed multiple clusters of related methanogens. Accordingly, a combination of antibodies targeting individual strains may be the most appropriate, broad spectrum approach to reduce methane production. Our findings support this hypothesis as the most substantial reduction of methane resulted from our Combo treatment containing antibodies against three strains each identified as being a member of a different discrete phylogenetic group.

These findings indicate that high titer, specific anti-methanogen avian antibodies can be generated following immunization of chickens with optimal dose of methanogen formulated with an appropriate adjuvant, MONTANIDE ISA 70 (mineral oil adjuvant), and the anti-methanogen antibodies have the capacity to prevent methanogenesis in the rumen. Furthermore, the most dramatic effect on reduction of methane production has been achieved with the treatment with combination of the three anti-methanogen antibodies rather than single antibodies. Therefore, it was concluded that an intervention strategy can be developed using the avian anti-methanogen antibody combination to reduce ruminal methane emissions. There are several possible mechanisms that may allow antibodies to neutralize methanogenic activity, including: growth inhibition, impeded uptake of $CH_4$ precursors, agglutination, or inhibition of symbiotic interactions.

Results

No adverse reactions were observed in the hens in response to the primary or booster immunizations with antigenic preparations using methanogens formulated with the three different adjuvant. Strong anti-methanogen antibody responses were induced in hyperimmunized eggs, following immunizations of laying hens on day 0, 21, and 42, with $5 \times 10^9$ methanogens formulated with CFA/IFA, and the avian antibody titers were determined to be between 1:32,000-1:64,000. The avian antibody titers were further increased to 1:64,000-128,000, when two more boost immunizations were given to the chickens (FIG. 1A). The strongest avian antibodies were detected when laying hens were immunized with M stadtmaniae, followed by M. ruminantium. To determine if an optimal dose of methanogen required for induction of anti-methanogen antibody responses, in the second study, three groups of chickens were immunized with $2.5 \times 10^9$, $5 \times 10^9$ or $1.0 \times 10^{10}$ dose of M. ruminantium formulated with another potent adjuvant, Quil A, in order to generate stronger antibody responses. Interestingly, the antibody response were found to be similar with CFA, with antibody titer 1:64,000 using all three doses of methanogen; however, the antibody responses were not further increased even after two more boost immunizations on day 84 and 133. Surprisingly, with higher dose of methanogen, the antibody responses were found to be lower on day 91 onwards (FIG. 1B). Therefore, hyperimmunized eggs were collected from laying hens after boost immunizations with CFA/IFA and utilized for preparation of purified avian antibodies. Finally, the purified antibodies were used to assess their function on methane reduction in in vitro fermentation in Experiment 1.

Experiment 1

None of the purified antibody treatments decreased $CH_4$ production over the duration of the experimental period compared with the non-immune control (Table 1). Cumulative $CH_4$ produced was similar at each sampling point, with $27.03 \pm 0.205$ mg g$^{-1}$ DM $CH_4$ produced after 24 h incubation. A slight depression of total gas produced was noted in the α-RUM treatment after 2 h and in the α-STAD treatment after 2 and 12 h. However, total gas produced recovered to become similar ($P=0.86$) among all treatments by the end of the incubation period (Table 1). Net ammonia and pH measures were also similar throughout the experimental duration ($P>0.05$). Likewise, IVDMD was not affected by specific antibody treatments ($P=0.91$).

Total VFA concentrations were similar between control and treatment groups ($P=0.63$). Equal proportion of acetate, propionate, butyrate and minor VFA were detected in control and treatment groups (Table 1), suggesting that the VFA profile was unaltered by treatment with specific anti-methanogen antibodies.

Subsequently, to achieve higher antibody responses against each of each of the three methanogens, three groups of laying hens were immunized with $5 \times 10^9$ of methanogen, M. ruminantium, M. smithii or M stadtmaniae formulated with another adjuvant, MONTANIDE ISA 70 (mineral oil adjuvant). Interestingly, after three immunizations on day 0, 21 and 42, the anti-methanogen antibody responses were found to stronger than previous two adjuvant formulation, with antibody titers between 1:64,000-1:256,000. The highest avian antibody titers were induced with M stadtmaniae, followed by M. ruminantium and M. smithii (FIG. 1C). Therefore, the anti-methanogen antibodies generated from eggs of the laying hens immunized with methanogens formulated with MONTANIDE ISA 70 (mineral oil adjuvant) were utilized to prepare avian antibodies by freeze-drying of hyperimmunized eggs. Subsequently, the antibodies were used to assess cross-reactivity of anti-methanogen antibodies, binding characteristics of methanogens present in ruminant fluid, and the functional activities of avian antibodies on reduction of methane gas, as individual antibody and combination of the three antibodies in the Experiment 2.

It was determined by ELISA that anti-M. ruminantium antibodies showed strong reactivity against homologous methanogen, *M. ruminantium* but weak reactivity against heterologous methanogens, *M stadtmaniae* and *M. smithii*. In contrast, anti-*M stadtmaniae* antibodies demonstrated strong reactivity against *M stadtmaniae* as well as heterologous methanogens, *M. smithii* and *M. ruminantium*. When, anti-*M. smithii* antibodies showed reactivity against homologous methanogen, *M. smithii* and similar degree of reactivity to heterologous methanogens *M stadtmaniae* than *M. ruminantium*. Thus, anti-*M stadtmaniae* antibodies were demonstrated to be the most cross-reactive anti-methanogen antibodies, followed by *M. smithii* (Table 2).

The similarities and difference between the three methanogens were further conformed by cross-absorption experiments. The *M stadtmaniae* antibody was used for cross-absorption study. It was determined by ELISA that when anti-*M. stadtmaniae* antibodies were absorbed with *M stadtmaniae*, about 80% of the antibody activity against *M stadtmaniae, M. smithii* and *M. ruminantium* was removed, when compared the reactivity of non-absorbed antibody. In contrast, when, anti-*M. stadtmaniae* antibody was absorbed with *M. smithii*, only 13%, 49% and 68% of anti-*M. stadtmaniae*, anti-*M. ruminantium* and anti-*M. smithii* antibody activity respectively, was removed. Therefore, considerable amounts of residual antibody remained which strongly reacted with *M. stadtmaniae* and followed by *M. ruminantium*. Similarly, when, anti-*M. stadtmaniae* antibody was absorbed with *M. ruminantium*, considerable amounts of residual antibody remained, which strongly reacted with *M. stadtmaniae*, followed by *M. smithii* and *M. ruminantium* (Table 3). Thus, it was confirmed that anti-*M. stadtmaniae* antibody was the most cross-reactive and a common antigen is found to be expressed by the three methanogens, *M. stadtmaniae, M. ruminantium* and *M. smithii*, which can be recognized by the anti-*M. stadtmaniae* antibodies.

Experiment 2

As ruminant fluid was used as source of methanogens in in vitro fermentation process in Experiment 2, to assess the effect of anti-methanogen antibodies on methane production, it was considered to be important to determine if anti-methanogen antibodies recognize methanogens present in the ruminant fluid. To confirm that the ruminant fluid contains methanogens, the reactivity of ruminant fluid was tested by ELISA against the three anti-methanogen antibodies. It was demonstrated from the results that all three anti-methanogen antibodies showed strong reactivity against the ruminant fluid, a reactivity similar to the homologous antigen. Again, the strongest reactivity was obtained with the anti-*M. stadtmaniae* antibodies, followed by anti-*M. smithii* and anti-*M. ruminantium* antibodies (Table 4). Thus, it was confirmed that ruminant fluid contains at least the target methanogens.

Figure 2:
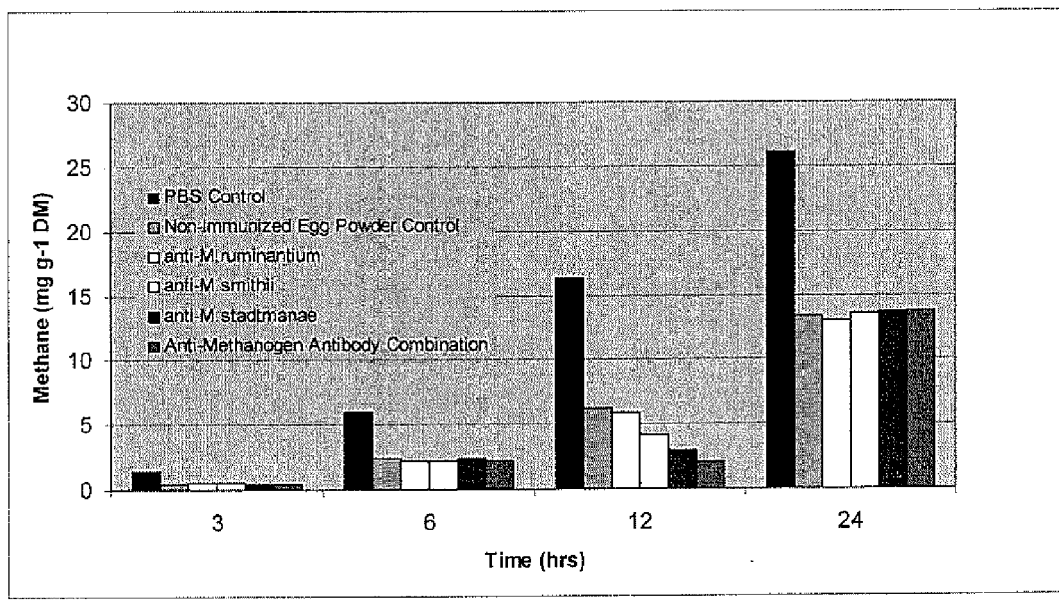
FIG. 2. Effect of the treatment with PBS, non-immunized egg powder (antibody control) and specific anti-methanogen antibodies (individually and three antibodies in combination) on methane production in in vitro ruminal fermentation FIG. 3. Percent reduction of methane gas production by treatment of ruminant fluid with specific anti-methanogen antibodies individually and three antibodies in combination, compared to the PBS control, in in vitro ruminal fermentation FIG. 4. Percent reduction of methane gas production at 12 hour post-treatment of ruminant fluid with specific anti-methanogen antibodies individually and three antibodies in combination in in vitro ruminal fermentation, compared to the antibody control (from non-immunized eggs).
Figure 3:
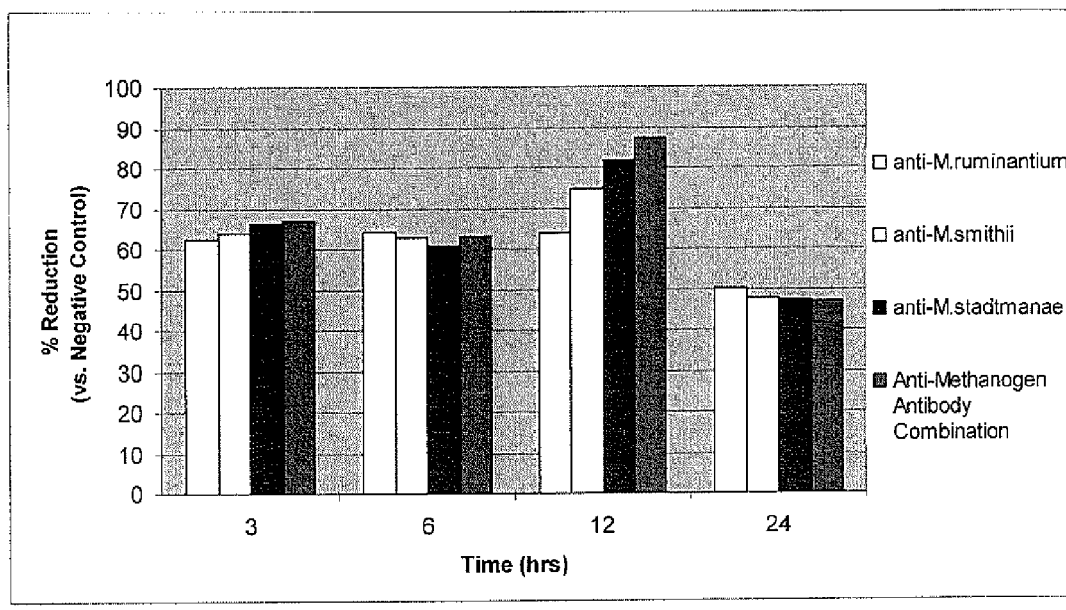
Figure 4:
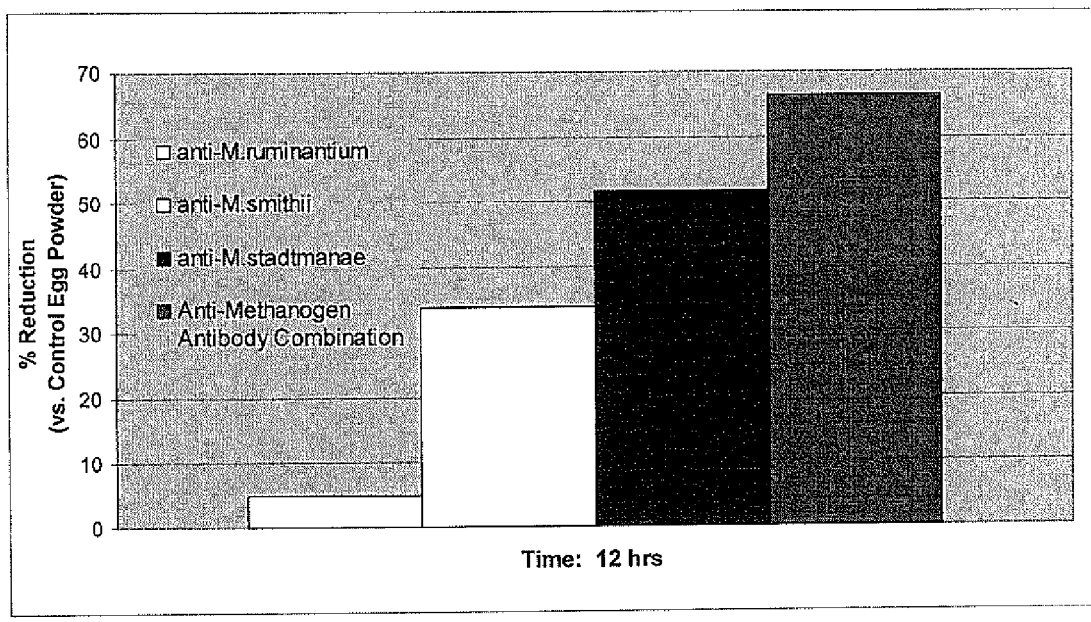

The effects of avian antibody on in vitro fermentation are summarized in Table 5. Three of the treatments (anti-*M. stadtmaniae, M. smithii* and Combo) had a significant positive effect, on methane production at 12 h (P≦0.05), compared with the antibody control. Furthermore, a significant reduction in methane production was achieved with all four treatments, when compared with the PBS control (FIG. 2). Of the treatments with a positive effect on methanogenesis, the anti-*M. stadtmaniae* and antibody-combo treatment groups had the most substantial effect, with greater than 60% reduction in methane production, compared to antibody control and more than 80% reduction in methane production, compared to PBS control, at 12 hours (FIGS. 3 and 4).

Individual anti-methanogen antibody treatments had unique effects on other fermentation measures including VFA. The same treatments exhibiting a positive effect on methane concurrently yielded less accumulated ammonia than the control (P<0.05; Table 2). Gas production and pH were sporadically different from the control, with no apparent trend to these effects. At 12 h, only the treatments with significant impacts on methane production exhibited differences in the proportion of VFA (data not shown). In particular, the α-STAD treatment was significantly different (P≦0.05) in every measure except acetate production. The VFA profile was positively shifted in each of these treatments at 12 h, such that proportion of propionate increased while acetate, butyrate and minor VFA decreased.

To account for basal inhibition of fermentation as a result of the copious doses of treatment (substrate), we conducted a comparison of the PBS control (no egg powder) to the antibody control (egg powder from unimmunized chicken). An extreme lag in gas production was observed in the antibody control (non-immune egg powder), yielding nearly 50% less gas at the conclusion of the in vitro incubation (Table 5, FIG. 2). Likewise, $CH_4$ production in the antibody control treatment was suppressed, about 50% compared with the PBS control. There were only slight variations in pH and net ammonia among the groups, except between 12 and 24 hours when the net ammonia in the antibody control exceeded the PBS control by 1.5-2.0 fold (Table 5).

We included a BES treatment in our analyses as a positive control for methanogen inhibition as earlier research has shown this compound to be a potent inhibitor of methanogenesis. Indeed, our results found that 250 μmol l$^{-1}$ dramatically reduced methane production throughout the experimental period, compared with the negative control, but also had adverse effects on overall fermentation.

Materials and Methods

Propagation of Methanogens

Three strains of methanogens were selected based on the characteristics of methanogens isolated from bovine rumen. *Methanobrevibacter smithii* PS was kindly provided by Rowett Institute. *Methanobrevibacter ruminantium* was obtained from the American Type Culture Collection (ATCC 35063), and *Methansphaera stadtmanae* was obtained from the Deutsche Sammlung von Mikrooganisem und Zellkulturen (DSMZ 3091; Braunschweig, Germany).

Cultures were maintained in 16×100 mm Hungate tubes in 5 mL of Methanomicrobium mobile medium (DSMZ), modified to include 1% methanol and 0.2% sodium formate (mM), at 39° C. Gas atmosphere of tubed media was 80% $H_2$/20% $CO_2$ at approximately 1.5 atmospheres. For vaccine preparation 6×600 mL of mM were inoculated with 5 mL aliquots of 3-4 day old cultures of each methanogen strain. Bottles were flushed daily with 80% $H_2$/20% $CO_2$ since pressurizing of media bottles was not possible. Cultures were harvested after 5-6 days of growth at 39° C. and collected by centrifugation at 21,800×g for 25 min, frozen at −70° C. and then freeze-dried.

Vaccination of Chickens and Generation of Avian Antibodies

Nine groups of five 24-25-week old laying hens were immunized in their pectoral muscle with methanogen emulsified with appropriate adjuvant. Three groups were immunized with 5×10$^9$ *M stadtmaniae, M. ruminantium* or *M. smithii*, emulsified with equal volume of CFA for the first immunization on day 0, and incomplete Freund's adjuvant for all subsequent immunizations, on day 21, 42, 84 and 133. Another three groups of chickens were immunized with 2.5× 10$^9$, 5×10$^9$ or 1.0×10$^{19}$ *M. ruminantium*, mixed with equal volume of Quil A (Cedarlane Lab. ON.), on days 0, 21, 42, 84 and 133. The remaining three groups of hens were immunized with 5×10$^9$ *M stadtmaniae, M. ruminantium* or *M. smithii* emulsified with MONTANIDE ISA 70 (mineral oil adjuvant) (SEPPIC, France) on day 0, 21 and 42. All hens were observed throughout the experimental period to determine if there are any adverse reactions following vaccinations. Hyperimmunized eggs were collected after immunizations to monitor induction of antibody responses against each of the methanogen. Hyperimmunized eggs collected at 1-3 week post-third immunization were used for preparation of purified antibodies as well as antibodies in freeze-dried egg powder for use in characterization of antibodies and determining their effect on methane production. Eggs collected prior to immunization with methanogens were used to generate antibody control, non-immunized egg powder.

Antibodies were purified from yolks of hyperimmunized as well as non-immunized eggs, following the method (17), with some modifications. Yolks were separated from the egg white and frozen at $-20°$ C. until further processing. After thawing, the yolks were diluted 1:10 in sterile distilled water and thoroughly mixed. The yolk solution was again frozen at $-20°$ C. overnight and thawed at 4° C. The yolk solution was then centrifuged at 10,000×g for 20 min, and the supernatant was filtered through Whatman #1 filters to clarify the solution. Finally, IgY was precipitated with ammonium sulphate and dialyzed against water. Protein concentration of purified IgY preparation was determined by the bicinchoninic acid method. Total IgY concentration was determined by a sandwich ELISA, the purity of the IgY sample was analyzed by SDS-PAGE and the purified IgY preparations were stored at $-20°$ C. until use.

Measurement of Antibody Activity

An ELISA method was developed, following some changes of the method ( ), to monitor induction of specific anti-methanogen avian antibody responses, to measure cross-reactivity of anti-methanogen antibodies and determine reactivity of ruminant fluid against anti-methanogen antibodies. Briefly, 96-well micro titer plates (Immulon 2, Dynatech Laboratories Inc, Chantilly, Va.) were coated with 100 µL/well of 0.005% poly-L-lysine (SIGMA) in phosphate-buffered saline (PBS) for 1 hour at 37° C. The plates were washed three times with PBS, coated with $1.0 \times 10^7$ *M stadtmaniae*, *M. ruminantium*, *M. smithii* or ruminant fluid in PBS containing 2.5% glutaraldehyde and incubated overnight at 2-8° C. Following incubation, the plates were washed three times with PBS containing 0.05% Tween 20 (PBST), and blocked with 5% skim milk (200 µL/well) for 1 hour at 37° C. The plates were washed three times with PBST and incubated with antibody samples (100 µL/well) for 2 hour at 37° C. Antibody samples were prepared by mixing 0.1 g of egg powder with 0.9 ml of PBS, and subsequently 2-fold dilutions were made. Following incubation, the plates were washed three times with PBST and then incubated for 1 hour at 37° C. with 100 µL/well of alkaline phosphatage-conjugated rabbit anti-chicken IgG (ImmunoJackson), diluted 1:5000 in PBS. The plates were washed three times with PBST, and incubated for 30 min at 37° C. with 100 µL/well of freshly prepared Sigma 104 Phosphatase Substrate. The absorbance was measured in a micro plate reader at a wavelength of 405 nm. Antibody titer was defined as the highest dilution of any sample that provides a positive reactivity, above the average blank +2SD.

Cross-Absorption

Cross-absorptions were carried out with a bacterial pellet prepared by washing 0.5 mg of freeze-dried methanogens with PBS. One of anti-*M stadtmaniae* antibodies at 1:1000 dilutions was suspended with washed pellet of each methanogen, *M stadtmaniae*, *M. ruminantium*, or *M. smithii* and the mixture was incubated for 6 hours at room temperature. The methanogens were then pelleted again, and the absorbed antibodies were recovered by centrifugation at 14,000 RPM for 5 min. Subsequently, the reactivity of the absorbed antibodies was determined by evaluating their binding characteristics to homologous methanogen, *M stadtmaniae* and heterologous methanogens, *M. ruminantium*, and *M. smithii* in ELISA.

Effect of Avian Antibody on Methane Production in In Vitro Batch Culture Fermentation Experiment 1

In vitro ruminal incubation was conducted to assess methane, volatile fatty acids (VFA) and ammonia production as well as in vitro dry matter digestibility (IVDMD) in the presence of antibody treatments. On the day before the incubation, 0.5 g of a total mixed ration (TMR) sample was weighed into 50 mL serum vials with rubber septa (six replicates per treatment for each of four sampling times). The TMR was freeze-dried and ground through a 1-mm screen for use in the assays and contained 46.5% forage and 53.5% concentrate (DM basis) and was typical of the diet fed to dairy cows in early lactation (18% CP; 33% NDF). On the day of incubation, equal volumes (400 µL) of three semi-purified antibodies from eggs of hens immunized with one of the three antigenic preparations with CFA (10 mg mL$^{-1}$ IgY) were dispensed into six replicate vials per treatment α(α-SMIT$^{CFA}$, α-RUM$^{CFA}$ or α-STAD$^{CFA}$). Additionally, a treatment containing an equal volume of semi-purified antibodies from eggs of non-immunized hens was included as a antibody control. Triplicate bottles containing no substrate were also prepared for each time point as controls for gas production and correction for IVDMD measures. In vitro ruminal incubation was conducted as previously described by Chaves et al. (2006).

After 2, 6, 12 and 24 h of incubation, six replicates of each treatment were removed from the incubator. Total gas production, methane determinations, and pH were measured at each sampling interval, and after 24 h samples were analyzed for VFA and ammonia, as described by Fraser et al. (2007).

The contents of three replicate bottles were transferred into pre-weighed 50 mL centrifuge tubes, rinsed and centrifuged twice at 600×g for 10 min at 4° C. Supernatants were discarded and precipitates (n=3) were dried at 55° C. for 48 h and weighed to estimate IVDMD.

Experiment-2

The same in vitro ruminal incubation techniques described for Trial 1 were used with the following modifications. On the day prior to incubation 0.6 g of antibody (12 mg of IgY) in freeze-dried egg powder from hens immunized with one of the three antigenic preparations with MONTANIDE ISA 70 (α-RUMI, α-SMIT, α-STAD), or a mixture of all three antibodies (Combo) was weighed into triplicate vials per treatment for each of the sampling times and stored overnight at 4° C. Equal quantities (0.2 g) of each egg powder preparation were represented in the antibody combo treatment. At the same time, freeze-dried alfalfa (28.1% CP and 41.6% NDF) ground to 1-mm was weighed into the serum vials. Ruminal fluid inoculum was collected from three dairy cows fed a TMR diet (16.7% CP, 34.4% NDF) consisting of 46% of a concentrate (20.5% canola, 20.4% soybean meal, 17% corn gluten meal, 14% barley ground, 12% beet pulp, 6.4% dried molasses, and 9.7% minerals), 41.5% whole crop barley silage, 7.5% corn grain, and 5% alfalfa hay, on dry matter basis. On the day of incubation, 100 µL of 50 mmol l$^{-1}$ 2-bromoethanesulfonic acid (BES) was dispensed into three replicate vials for each sampling time. This treatment of BES was excluded from statistical analyses due to substantial differences in the dry matter incubated, affecting the overall digestive fermentation. The presence of methanogens in the ruminal fluid was assessed by testing the reactivity against each of the three anti-methanogen antibodies, described.

All digestive fermentation parameters, including ammonia and VFA production were measured from samples collected at 3, 6, 12 and 24 h. Analyses were conducted as in Trial 1, except only 3 replicate vials were incubated and so headspace gas was removed for methane analysis prior to total gas determination. All samples were corrected for gas and IVDMD compared with no substrate controls (blanks).

While the preferred embodiments of the invention have been described above, it will be recognized and understood that various modifications may be made therein, and the appended claims are intended to cover all such modifications which may fall within the spirit and scope of the invention.

REFERENCES

Canadian Council on Animal Care, 1993. Guide to the care and use of experimental animals. Volume 1. E. D. Olfert, B. M. Cross, and A. A. McWilliams, eds. CCAC, Ottawa, ON. 212 pp.

Chaves, A. V.; Thompson, L. C.; Iwaasa, A.; Scott, S.; Olson, M. E.; Benchaar, C.; McAllister, T. A. and Veira, D. M. 2006. Effect of pasture type (alfalfa vs. grass) on methane and carbon dioxide production by yearling beef heifers. Can. J. Anim. Sci. 86: 409-418.

Clark, C. K., Petersen, M. K., Newman, C. W., McInerney, M. J. and Wiley, J. S. 1987. Evaluation of in vitro dry matter, neutral detergent fibre and crude protein fermentation rate of normal, proanthocyanidin-mutant and cross-line barley. Proc. West. Sect., Amer. Soc. Anim. Sci. 38: 293-296.

Fedorak, P. M. and Hrudey, S. E. 1983. A simple apparatus for measuring gas production by methanogenic cultures in serum bottles. Environ. Technol. Lett. 4: 425-432.

Fraser, G.; Chaves, A. V.; Wang, Y.; McAllister, T. A.; Beauchemin, K. A. and Benchaar, C. 2007. Assessment of the effects of cinnamon leaf oil on rumen microbial fermentation using two continuous culture systems. J. Dairy Sci.: in press.

Johnson, K. A. and Johnson, D. E. 1995. Methane emissions from cattle. J. Anim. Sci. 73: 2483-2492.

Kassaify, Z. G. and Mine, Y. 2004. Nonimmunized egg yolk powder can suppress the colonization of Salmonella typhimurium, Escherichia coil O0157:H7, and Campylobacter jejuni in laying hens. Poult. Sci. 83:1497-1506.

Menke, K. H., Raab, L., Salewski, A., Steingass, H., Fritz, D. and Schneider, W. 1979. The estimation of the digestibility and metabolizable energy content of ruminant feedingstuffs from the gas production when they are incubated with rumen liquor in vitro. J Agric Sci (Camb) 93: 217-222.

McAllister, T. A., Okine, E. K., Mathison, G. W., Cheng, K.-J. 1996. Dietary, environmental and microbiological aspects of methane production in ruminants. Can J. Anim. Sci. 76: 231-243.

SAS Institute Inc. 2006. SAS OnlineDoc® 9.1.3. Cary, N.C.: SAS Institute Inc.

Wang, Y., McAllister, T. A., Xu, Z. J., Gruber, M. Y., Skadhauge, B., Jende-Strid, B. and Cheng, K-J. 1999. Effects of proanthocyanidins, dehulling and removal of pericarp on digestion of barley grain by ruminal microorganisms. J. Sci. Food Agric. 79: 929-938.

Weatherburn, M. W. 1967. Phenol-hypochlorite reaction for determination of ammonia. Anal. Chem. 39: 971-974.

Whitford, M. F., Teather, R. M., Forster, R. J. 2001. Phylogenetic analysis of methanogens from the bovine rumen. BMC Microbiol. 1: pgs Wright, A. D. G., Kennedy, P., O'Neill, C. J., Toovey, A. F., Popovski, S., Rea, S. M., Pimm, C. L., Klein, L. 2004. Reducing methane emissions in sheep by immunization against rumen methanogens. Vaccine. 22: 3976-3985.

TABLE 1

Effects of semi-purified specific anti-methanogen IgY antibodies on fermentation characteristics of in vitro ruminal batch culture. n = 3 (Trial 1)

| Parameter | Time | Treatment | | | | SE | Level of Significance | |
|---|---|---|---|---|---|---|---|---|
| | | CONTROL | α-RUM$^{CFA}$ | α-SMI$^{CFA}$ | α-STAD$^{CFA}$ | | Treat | Adj. P≦ |
| Total Gas | 2 | 31.96 | 33.94 | 34.95* | 36.85* | 0.472 | <0.001 | 0.004 |
| (mL g$^{-1}$ DM) | 6 | 96.78 | 98.63 | 99.31 | 99.74 | 0.884 | 0.178 | |
| | 12 | 155.40 | 158.02 | 156.74 | 156.95* | 1.141 | 0.034 | 0.012 |
| | 24 | 196.85 | 197.69 | 198.03 | 198.82 | 3.397 | 0.862 | |
| pH | 2 | 6.73 | 6.71 | 6.72 | 6.72 | 0.006 | 0.304 | |
| | 6 | 6.32 | 6.34 | 6.30 | 6.32 | 0.014 | 0.195 | |
| | 12 | 5.93 | 5.96 | 5.94 | 5.98 | 0.019 | 0.369 | |
| | 24 | 5.72 | 5.63 | 5.66 | 5.67 | 0.027 | 0.163 | |
| Methane | 2 | 1.05 | 1.13 | 1.11 | 1.15 | 0.045 | 0.197 | |
| (mg/g DM) | 6 | 7.62 | 8.54 | 8.90 | 8.68 | 0.290 | 0.079 | |
| | 12 | 16.86 | 18.04 | 17.46 | 18.11 | 0.896 | 0.572 | |
| | 24 | 27.00 | 26.80 | 27.30 | 27.03 | 0.430 | 0.297 | |
| Ammonia (mmol l$^{-1}$) | 24 | 6.98 | 3.89 | 5.23 | 7.47 | 1.239 | 0.134 | |
| IVDMD | 24 | 0.38 | 0.38 | 0.38 | 0.38 | 0.006 | 0.910 | |
| VFA, mol % | | | | | | | | |
| Acetate(C2) | 24 | 0.54 | 0.52 | 0.52 | 0.53 | 0.010 | 0.665 | |
| Propionate (C3) | 24 | 0.22 | 0.23 | 0.23 | 0.23 | 0.003 | 0.439 | |
| Butyrate | 24 | 0.17 | 0.18 | 0.18 | 0.17 | 0.006 | 0.715 | |
| Minor VFA | 24 | 0.07 | 0.07 | 0.07 | 0.06 | 0.003 | 0.366 | |
| Ratio C2:C3 | 24 | 2.45 | 2.26 | 2.26 | 2.30 | 0.070 | 0.627 | |
| Total VFA (mM) | 24 | 127.59 | 123.82 | 121.16 | 130.73 | 4.704 | 0.632 | |

IVDMD, in vitro dry matter digestibility.
Adj. P: minimal significance level difference among least square means adjusted by Dunnett's test (all treatments compared to control)
*Indicates a significant difference between Treatment and CONTROL

TABLE 2

Measurement of the cross-reactivity between *M. ruminatium*, *M. smithii* and *M. stadtmanae* by ELISA Reactivity ($A_{405nm}$ ± SD) of Anti-methanogen antibodies at 1:8000 dilution

| Antigen (methanogen) | Anti-*M. ruminatium* | Anti-*M. smithii* | Anti-*M. stadtmanae* |
|---|---|---|---|
| *M. ruminatium* | 1.02 ± 0.02 | 0.4 ± 0.01 | 0.88 ± 0.07 |
| *M. smithii* | 0.27 ± 0.00 | 0.5 ± 0.00 | 0.81 ± 0.02 |
| *M. stadtmanae* | 0.27 ± 0.00 | 0.38 ± 0.00 | 0.8 ± 0.03 |

TABLE 3

Quantitative estimation of relatedness between the three methanogens determined with absorbed antibodies ELISA reactivity of Anti-*M. stadtmanae* antibody absorbed with[1]

| Antigens (methanogens) | Nothing | *M. stadtmanae* ($A_{405\ nm}$) | Percent Reduction | *M. ruminatium* ($A_{405\ nm}$) | Percent Reduction | *M. smithii* ($A_{405\ nm}$) | Percent Reduction |
|---|---|---|---|---|---|---|---|
| *M. ruminatium* | 0.83 | 0.16 | 80.7 | 0.18 | 78.3 | 0.42 | 49.4 |
| *M. smithii* | 1.16 | 0.25 | 78.4 | 0.28 | 75.9 | 0.37 | 68.1 |
| *M. stadtmanae* | 1.36 | 0.27 | 80.1 | 0.73 | 46.3 | 1.18 | 13.2 |

TABLE 4

ELISA Reactivity of anti-methanogen antibodies to methanogens in ruminant fluid

Reactivity ($A_{405nm}$ ± SD) of Anti-methanogen antibodies at 1:16,000 dilution

| Antigen (methanogen) | Anti-*M. ruminatium* | Anti-*M. smithii* | Anti-*M. stadtmanae* |
|---|---|---|---|
| *M. ruminatium* | 0.59 ± 0.06 | | |
| *M. smithii* | | 0.47 ± 0.02 | |
| *M. stadtmanae* | | | 1.07 ± 0.00 |
| Ruminant fluid | 58 ± 0.05 | 0.64 ± 0.01 | 1.01 ± 0.01 |

TABLE 5

Effects of 0.6 g of egg powder containing specific anti-methanogen antibodies on fermentation characteristics of in vitro ruminal batch culture. n = 3 (Trial 2)

| Parameter | Time | Negative Control | CONTROL | α-RUM | α-SMI | α-STAD | COMBO | SE | Treat | Adj. P ≤ |
|---|---|---|---|---|---|---|---|---|---|---|
| Total Gas (mL g$^{-1}$ DM) | 3 | 45.69[††] | 18.05 | 18.70 | 18.83 | 18.10 | 18.14 | 0.295 | 0.253 | |
| | 6 | 101.24[††] | 45.36 | 44.20 | 44.66 | 45.22 | 44.31 | 0.637 | 0.625 | |
| | 12 | 155.17[††] | 71.83 | 68.19 | 62.55 | 57.56* | 59.49 | 3.254 | 0.054 | 0.036 |
| | 24 | 192.23[††] | 102.81 | 100.03* | 101.24 | 102.46 | 103.13 | 0.677 | 0.046 | 0.048 |
| pH | 3 | 6.33 | 6.32 | 6.37* | 6.32 | 6.32 | 6.36 | 0.013 | 0.026 | 0.045 |
| | 6 | 6.20 | 6.20 | 6.21 | 6.22 | 6.20 | 6.22 | 0.009 | 0.445 | |
| | 12 | 6.06[†] | 5.99 | 5.96* | 5.96* | 5.98 | 6.02 | 0.007 | 0.001 | 0.020 |
| | 24 | 6.05[†] | 6.30 | 6.26* | 6.28 | 6.30 | 6.30 | 0.005 | <0.001 | <0.001 |
| Methane (mg g$^{-1}$ DM) | 3 | 1.46[††] | 0.46 | 0.55* | 0.53* | 0.49 | 0.48 | 0.013 | 0.005 | 0.011 |
| | 6 | 6.02[††] | 2.38 | 2.16 | 2.23 | 2.36 | 2.22 | 0.095 | 0.447 | |
| | 12 | 16.33[††] | 6.20 | 5.90 | 4.10* | 3.00* | 2.08* | 0.391 | <0.0001 | 0.011 |
| | 24 | 26.02[††] | 13.33 | 13.00 | 13.57 | 13.65 | 13.76 | 0.173 | 0.069 | |

TABLE 5-continued

Effects of 0.6 g of egg powder containing specific anti-methanogen antibodies on fermentation characteristics of in vitro ruminal batch culture. n = 3 (Trial 2)

| Parameter | Time | Treatment | | | | | | SE | Level of Significance | |
| --- | --- | --- | --- | --- | --- | --- | --- | --- | --- | --- |
| | | Negative Control | CONTROL | α-RUM | α-SMI | α-STAD | COMBO | | Treat | Adj. P ≦ |
| Ammonia | 3 | 7.14 | 5.97 | 5.91 | 7.24 | 6.36 | 5.77 | 0.605 | 0.469 | |
| (mmol l$^{-1}$) | 6 | 10.62 | 10.46 | 10.56 | 9.94 | 8.73 | 7.75 | 0.912 | 0.213 | |
| | 12 | 20.97 | 23.30 | 18.22 | 13.29* | 10.45* | 10.69* | 1.495 | 0.001 | 0.003 |
| | 24 | 37.33†† | 71.46 | 63.34 | 59.82* | 70.20* | 71.12* | 2.053 | 0.007 | 0.008 |
| IVDMD | 24 | 0.43†† | 0.64 | 0.64 | 0.60 | 0.63 | 0.63 | 0.012 | 0.270 | |
| VFA, mol % | | | | | | | | | | |
| Acetic (C2) | 24 | — | 0.48 | 0.52 | 0.50 | 0.51 | 0.49 | 0.009 | 0.056 | |
| Propionic (C3) | 24 | — | 0.31 | 0.30 | 0.31 | 0.31 | 0.32 | 0.003 | 0.092 | |
| Butyrate | 24 | — | 0.10 | 0.08* | 0.09 | 0.08* | 0.09 | 0.003 | 0.040 | 0.039 |
| Minor VFA | 24 | — | 0.11 | 0.09* | 0.10 | 0.10* | 0.10 | 0.004 | 0.017 | 0.039 |
| Ratio (C2:C3) | 24 | — | 1.55 | 1.73 | 1.61 | 1.65 | 1.53 | 0.041 | 0.078 | |
| Total VFA (mmol l$^{-1}$) | 24 | — | 168.30 | 154.97* | 155.76* | 163.29 | 162.10 | 1.758 | 0.002 | 0.002 |

IVDMD, in vitro dry matter digestibility.
Adj. P: minimal significance level difference among least square means adjusted by Dunnett's test (all treatments compared to control)
*Indicates a significant difference between Treatment and CONTROL
†Indicates a significant difference between Negative control and CONTROL (P ≦ 0.01)
††Indicates a significant difference between Negative control and CONTROL (P ≦ 0.001)

The invention claimed is:

1. A method of reducing methane gas production from a ruminant animal comprising:

immunizing hens with methane-producing *M. stadtmaniae* methanogens administered with MONTANIDE ISA 70 (mineral oil adjuvant);

drying IgY antibodies from eggs from said immunized hens into a powder, thereby producing an egg powder, said egg powder having an *M. stadtmaniae* antibody titer of at least 1:64000; and administering to said animal an effective amount of said egg powder comprising anti-*M. stadtmaniae* antibodies, thereby reducing methane gas evolved by said animal compared to an untreated or mock treated control animal of similar age and condition.

2. The method according to claim 1 wherein the egg powder administered to the animal is a mixture further comprising anti-*M ruminantium* antibodies from eggs of hens immunized with methane producing *M. ruminantium* methanogens administered with MONTANIDE ISA 70 (mineral oil adjuvant) or *M smithii* antibodies from eggs of hens immunized with methane producing *M smithii* methanogens administered with MONTANIDE ISA 70 (mineral oil adjuvant).

* * * * *